(12) United States Patent
Matza et al.

(10) Patent No.: US 10,745,303 B2
(45) Date of Patent: *Aug. 18, 2020

(54) PROCESS FOR DECONTAMINATION OF HAZARDOUS SULFUR COMPOUNDS IN SOUR WATER TANKS

(71) Applicant: United Laboratories International, LLC, Houston, TX (US)

(72) Inventors: Stephen D. Matza, Sugarland, TX (US); Jack G. Frost, Duncan, OK (US)

(73) Assignee: United Laboratories International, LLC, Houston, TX (US)

( * ) Notice: Subject to any disclaimer, the term of this patent is extended or adjusted under 35 U.S.C. 154(b) by 132 days.

This patent is subject to a terminal disclaimer.

(21) Appl. No.: 15/797,492

(22) Filed: Oct. 30, 2017

(65) Prior Publication Data

US 2018/0297874 A1    Oct. 18, 2018

Related U.S. Application Data

(63) Continuation of application No. 14/512,987, filed on Oct. 13, 2014, now Pat. No. 9,815,720, which is a
(Continued)

(51) Int. Cl.
*C02F 1/72* (2006.01)
*C10G 29/20* (2006.01)
(Continued)

(52) U.S. Cl.
CPC ............... *C02F 1/725* (2013.01); *C02F 1/02* (2013.01); *C02F 1/38* (2013.01); *C02F 1/68* (2013.01);
(Continued)

(58) Field of Classification Search
None
See application file for complete search history.

(56) References Cited

U.S. PATENT DOCUMENTS 5,053,138 A    10/1991   Korger et al.
5,611,932 A    3/1997    Lee et al.
(Continued)

FOREIGN PATENT DOCUMENTS

AU    2012322060    4/2013

OTHER PUBLICATIONS

Non Final Office Action for U.S. Appl. No. 14/512,987 dated Sep. 30, 2016.
(Continued)

*Primary Examiner* — Clare M Perrin
(74) *Attorney, Agent, or Firm* — Tumey L.L.P.

(57) ABSTRACT

A method and system treat contaminated water. In one embodiment, the method comprises treating contaminated water by introducing a methylmorpholine-N-oxide solution to a vessel. The vessel contains the contaminated water and iron oxide. The contaminated water comprises contaminants. In addition, the methylmorpholine-N-oxide solution comprises methylmorpholine-N-oxide and water. The method further comprises contacting the methylmorpholine-N-oxide solution with the contaminated water. In addition, the method comprises treating the contaminated water by allowing the methylmorpholine-N-oxide to react with the contaminants in the presence of the iron oxide.

20 Claims, 3 Drawing Sheets

Related U.S. Application Data continuation of application No. 13/650,561, filed on Oct. 12, 2012, now Pat. No. 9,512,019.

(60) Provisional application No. 61/546,481, filed on Oct. 12, 2011.

(51) Int. Cl.
| | |
|---|---|
| *C10G 29/04* | (2006.01) |
| *C02F 1/68* | (2006.01) |
| *C02F 1/38* | (2006.01) |
| *C02F 1/02* | (2006.01) |
| *C07D 265/32* | (2006.01) |
| *E21B 43/34* | (2006.01) |
| *E21B 21/06* | (2006.01) |
| *C09K 8/532* | (2006.01) |
| *C02F 101/10* | (2006.01) |
| *C02F 103/36* | (2006.01) |

(52) U.S. Cl.
CPC .............. *C10G 29/04* (2013.01); *C10G 29/20* (2013.01); *C02F 2101/101* (2013.01); *C02F 2103/365* (2013.01); *C02F 2209/02* (2013.01); *C02F 2305/02* (2013.01); *C07D 265/32* (2013.01); *C09K 8/532* (2013.01); *C09K 2208/20* (2013.01); *C10G 2300/207* (2013.01); *C10G 2300/807* (2013.01); *E21B 21/063* (2013.01); *E21B 43/34* (2013.01)

(56) References Cited

U.S. PATENT DOCUMENTS

| | | | | |
|---|---|---|---|---|
| 5,820,766 | A * | 10/1998 | Gevertz | B01D 53/52 210/753 |
| 5,967,230 | A | 10/1999 | Cooper et al. | |
| 5,980,733 | A * | 11/1999 | Collins | A62D 3/30 208/236 |
| 6,221,277 | B1 | 4/2001 | Scranton, Jr. | |
| 8,993,488 | B2 * | 3/2015 | Frost | C09K 8/52 507/103 |
| 9,512,019 | B2 | 12/2016 | Matza et al. | |
| 9,920,236 | B2 | 3/2018 | Matza et al. | |
| 2003/0217974 | A1 | 11/2003 | Uegami et al. | |
| 2007/0048212 | A1 | 3/2007 | Bierle et al. | |
| 2008/0053920 | A1 * | 3/2008 | Pakulski | B01D 53/485 210/749 |
| 2011/0272365 | A1 * | 11/2011 | DeFosse | C02F 1/20 210/750 |
| 2013/0140243 | A1 * | 6/2013 | Gustafsson | C02F 1/5236 210/722 |

OTHER PUBLICATIONS

Final Office Action for U.S. Appl. No. 14/512,987 dated Feb. 1, 2017.
EPO Notice of Allowance for European Application No. 12 839 497.0-1357 dated Aug. 6, 2016.
Australian Patent Examination Report No. 1 for Australian Patent Application No. 2012322060 dated Jul. 20, 2016.
International Search Report and Written Opinion for PCT/US12/59934 dated Dec. 24, 2012.
Notice of Allowance for U.S. Appl. No. 13/650,561 dated Jul. 7, 2014.
Extended European Search Report for EP 12839497 dated Aug. 11, 2015.
STIC Search Results for U.S. Appl. No. 13/650,561 received Jun. 23, 2014.
Notice of Allowance for U.S. Appl. No. 14/512,987 dated Jun. 10, 2017.
USPTO Issue Notification for U.S. Appl. No. 13/650,561 dated Nov. 16, 2016.
USPTO Issue Notification for U.S. Appl. No. 14/512,987 dated Oct. 25, 2017.
Australian Examination Report No. 1 for Application No. 2017206259, dated Nov. 7, 2018.

* cited by examiner

PROCESS FOR DECONTAMINATION OF HAZARDOUS SULFUR COMPOUNDS IN SOUR WATER TANKS

CROSS-REFERENCE TO RELATED APPLICATIONS

This application is a continuation of U.S. application Ser. No. 14/512,987 filed on Oct. 13, 2014 which is a continuation of U.S. Pat. No. 9,512,019 filed on Oct. 12, 2012 which is a non-provisional that claims the benefit of U.S. Application Ser. No. 61/546,481 filed on Oct. 12, 2011, all of which are incorporated by reference herein in their entirety.

STATEMENT REGARDING FEDERALLY SPONSORED RESEARCH OR DEVELOPMENT

Not applicable.

BACKGROUND OF THE INVENTION

Field of the Invention

This invention relates to the field of decontamination and more specifically to the field of decontaminating water in vessels using methylmorpholine-N-oxide.

Background of the Invention

Refineries and petrochemical plants are commonly contaminated with dangerous and reactive sulfur compounds such as $H_2S$ and pyrophoric iron sulfides. These compounds are typically mitigated or removed as part of decontamination procedures, for instance, prior to vessel (e.g., large storage tanks) entry by individuals. A conventional approach to decontamination is to use hydrogen sulfide scavengers (e.g., liquid scavengers) such as triazine, acrolein, or formaldehyde. Such scavengers may rely on non-oxidative complexation and may be an economical approach for $H_2S$ mitigation. Liquid scavengers may tie up $H_2S$ as water-soluble compounds that may be discharged to wastewater treatment facilities. However, such scavengers have drawbacks. For instance, some of the reaction products may not be water-soluble, and some of the treatment chemicals may have associated toxicity or environmental restrictions in certain locations. In addition, only acrolein typically neutralizes pyrophoric iron sulfides. Triazine treatments may raise the pH of effluent streams and as a result, may promote the formation of scales on metal surfaces. Formaldehyde reactions with $H_2S$ typically produce water insoluble products. Acrolein benefits may be tempered by its toxicity.

Other methods have been developed and demonstrated to be effective at oxidizing and eliminating $H_2S$ and pyrophoric iron sulfide. Such methods include using permanganate (e.g., potassium permanganate), persulfate, sodium nitrite, ozone, hypochlorite, adducts of peroxide such as perborates and percarbonates, and long-chain amine oxides. The oxidizing chemicals may irreversibly convert $H_2S$ to harmless water soluble forms of sulfur, which may be compatible with effluent discharge. Each of these scavengers and oxidizing compounds (i.e., oxidizing chemicals) have certain drawbacks. For instance, considering the strong oxidizers, persulfates may be corrosive. Hypochlorite may form dangerous chlorine compounds. Ozone and permanganate may require field mixing, and permanganate decontaminations may be further complicated by large amounts of reaction solids that are typically processed at additional cost. Sodium nitrite may produce ammonia as a by-product, which may stall the sulfide oxidation before it is complete. For perborates and percarbonates, field mixing or solutions prepared with stabilizing agents are typically used. Percarbonates, as with permanganate, may also be exothermic in their reaction, which may be particularly dangerous if hydrocarbon vapors are present. It is to be understood that long-chain amine oxides often include large volumes and may produce excessive foam. Permanganate produces solid manganese dioxide as a reaction product that is typically processed at added cost. Treatments using strong oxidizers are typically accomplished in small sequential batches outside the storage vessel in order to control the associated exotherm. As a result, these treatments may involve considerable time and therefore cost. However, these compounds may also react violently with hydrocarbon components that may be present in sour sludge. Strong oxidizers (i.e., permanganate, percarbonate, persulfate) may be quite non-selective in their reaction and may react with many of the hydrocarbon components that may exist in the sludge that typically is contained in storage vessels. As a result, these type treatments are typically accomplished in small sequential batches outside the vessel in time-consuming fashion.

Mild oxidizers such as amine oxides and nitrites may also be effective at irreversibly oxidizing hydrogen sulfide to harmless forms of sulfur while having limited or no effect on hydrocarbons, which is unlike the strong oxidizers. Such mild oxidizers may normally be added directly to the storage vessel since associated reactions are non-exothermic. Such mild oxidizers also have drawbacks. For instance, typical long-chain amine oxides may pose foaming issues due to their surfactancy. These amine oxides may also have limited efficiency for large amounts of $H_2S$, since they are typically diluted in water to prevent gel formation. Nitrites may also have drawbacks, as their reaction with hydrogen sulfide produces ammonia. As a result, the nitrite oxidation reaction may be accompanied by a rise in pH, which at some point may cease the oxidation before it is complete.

Consequently, there is a need for improved methods and products for decontaminating vessels such as sour water tanks.

BRIEF SUMMARY OF SOME OF THE PREFERRED EMBODIMENTS

These and other needs in the art are addressed in one embodiment by a method for treating contaminated water. The method includes introducing a methylmorpholine-N-oxide solution to a vessel. The vessel contains the contaminated water and iron oxide. The contaminated water comprises contaminants. The methylmorpholine-N-oxide solution comprises methylmorpholine-N-oxide and water. The method further comprises contacting the methylmorpholine-N-oxide solution with the contaminated water. In addition, the method comprises treating the contaminated water by allowing the methylmorpholine-N-oxide to react with the contaminants in the presence of the iron oxide.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
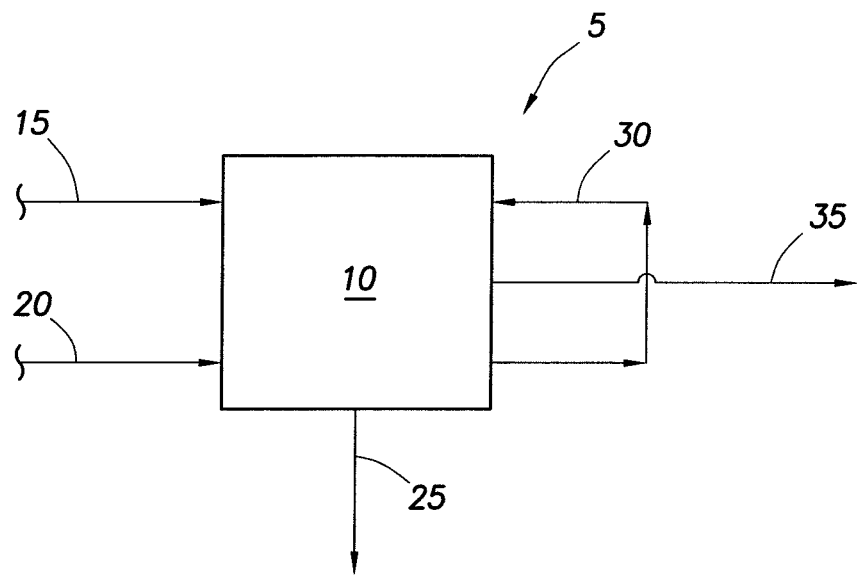
FIG. 1 illustrates an embodiment of a methylmorpholine-N-oxide water treatment method.

FIG. 1 illustrates an embodiment of methylmorpholine-N-oxide water treatment method 5. In an embodiment, methylmorpholine-N-oxide water treatment method 5 treats contaminated water by decontaminating the water by removing a portion or all of the contaminants from the water.

In embodiments as shown in FIG. 1, the contaminated water is disposed in a vessel 10. Vessel 10 may include any type of vessel that may contain water. In an embodiment, vessel 10 is a tank. In embodiments, the water is contaminated with contaminants. Without limitation, examples of contaminants include hydrogen sulfide, iron sulfides, or any combinations thereof. In an embodiment, the contaminant comprises hydrogen sulfide. In some embodiments, the iron sulfides comprises pyrophoric iron sulfides. The pyrophoric iron sulfides may include any pyrophoric iron sulfides. In embodiments, the pyrophoric iron sulfides comprise pyrite, troilite, marcasite, pyrrhotite, or any combinations thereof.

FIG. 1 shows an embodiment of methylmorpholine-N-oxide water treatment method 5 in which methylmorpholine-N-oxide 20 is introduced to vessel 10. Methylmorpholine-N-oxide 20 may be introduced to vessel 10 by any suitable means. Without limitation, examples of such suitable means include a drum pump, tank truck, and the like. Methylmorpholine-N-oxide 20 may be introduced in any suitable form for removing the contaminants from the contaminated water. In embodiments, methylmorpholine-N-oxide 20 is in a methylmorpholine-N-oxide solution comprising methylmorpholine-N-oxide and water. The methylmorpholine-N-oxide solutoin may have the methylmorpholine-N-oxide in any desired amount. In some embodiments, the methylmorpholine-N-oxide may be in a very concentrated form. Without being limited by theory, such very concentrated form may allow the methylmorpholine-N-oxide to be applied in small, efficient amounts. The concentrated form may include any desirable concentration. In an embodiment, the concentration of methylmorpholine-N-oxide in the water is between about 1 weight volume % and about 60 weight volume %, alternatively between about 10 weight volume % and about 20 weight volume %, further alternatively between about 5 weight volume % and about 60 weight volume %, and alternatively between about 50 weight volume % and about 60 weight volume %. In embodiments, the concentration of methylmorpholine-N-oxide in the water may be any individual weight volume % in the above ranges or any smaller range of weight volume % that is included in the above ranges. In an embodiment, the concentration of methylmorpholine-N-oxide in the water is between about 50 weight volume % and about 60 weight volume %. In an embodiment, the methylmorpholine-N-oxide is a short-chain amine oxide. In embodiments, the methylmorpholine-N-oxide has the molecular formula $C_5H_{11}NO_2$. In vessel 10, methylmorpholine-N-oxide 20 contacts the contaminated water. In embodimetns, methylmorpholine-N-oxide 20 is not heated before introduction to vessel 10. In embodiments, the amount of methylmorpholine-N-oxide 20 added to vessel 20 provides a mole ratio of methylmorpholine-N-oxide:hydrogen sulfide in vessel 20 from about 1.0 mole methylmorpholine-N-oxide:1.0 mole hydrogen sulfide to about about 3.0 mole methylmorpholine-N-oxide:1.0 mole hydrogen sulfide, or any range or mole ratio therebetween.

In further embodiments as shown in FIG. 1, steam 15 is also added to vessel 10. Steam 15 is added to increase the temperature of the contaminated water in vessel 10. In embodiments, steam 15 is added to vessel 10 in amounts to increase the temperature of the contaminated water to a temperature from about 75° F. to about 212° F., alternatively from about 90° F. to about 180° F., and alternatively from about 100° F. to about 140° F. In embodiments, the temperature may be any individual temperature in the above ranges or any smaller range of temperatures that is included in the above ranges. Any suitable psig steam may be used. In embodiments, the steam is 150 psig or less. In an embodiment, the steam is 50 psig steam or 150 psig steam.

Figure 3:
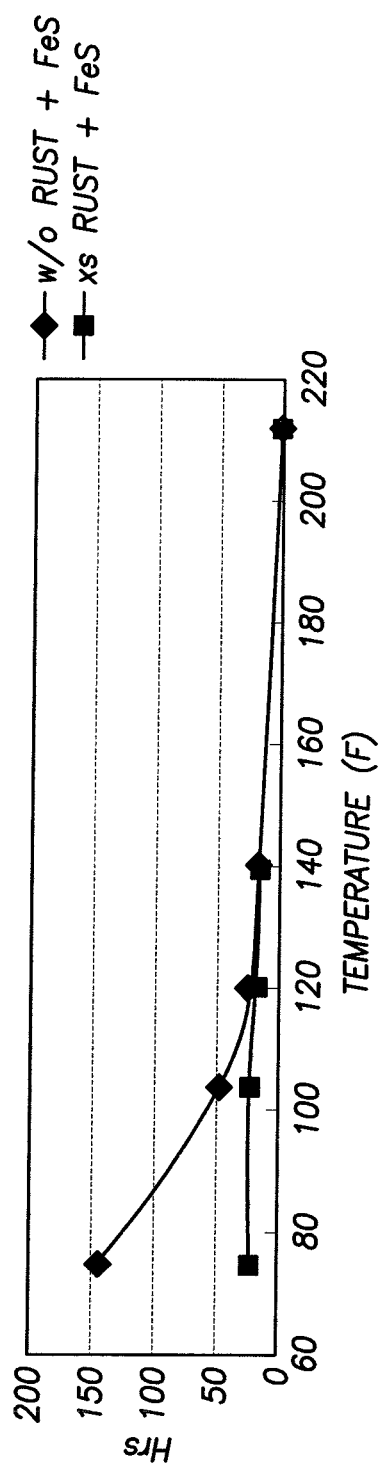
FIG. 3 illustrates reaction time versus temperature.

In embodiments, the methylmorpholine-N-oxide reacts with the contaminants in the presence of iron oxide (i.e., rust). Without being limited by theory, the presence of iron oxide catalyzes the amine oxide (i.e., methylmorpholine-N-oxide) to convert reactive sulfide to elemental sulfur and thiosulfate reaction products irreversibly. Any suitable iron oxide may be used. In embodiments, the iron oxide includes hydrated iron oxide, anhydrous iron oxide, or any combinations thereof. In an embodiment, the iron oxide is hydrous iron oxide. In embodiments, the iron oxide includes ferrous or ferric oxides that are hydrated. In an embodiment, the iron oxide is $Fe_2O_3 \cdot 7H_2O$, $Fe_2O_3 \cdot 10H_2O$, or any combinations thereof. The iron oxide may be present in vessel 10 in any amount suitable to catalyze the reaction between the amine oxide and the contaminants. In an embodiment, vessel 10 has iron oxide in the contaminated water in an amount from about 100 ppm iron oxide to about 1,000 ppm iron oxide. In embodiments, the iron oxide may be present in any individual amount in the above range or any smaller range of amounts that is included in the above range. In embodiments, no iron oxide is added to vessel 10 as methylmorpholine-N-oxide water treatment method 5 uses the iron oxide already present in vessel 10. In other embodiments, iron oxide is added to vessel 10. Without being limted by theory, the reaction to remove the contaminants (i.e., reactive sulfide) from the contaminated water comprises methylmorpholine-N-oxide, steam, and iron oxide. The reaction is allowed to occur for a sufficient time to allow the contaminants to be removed (i.e., converted) from the water. In embodiments, the reaction is allowed to occur from about one hour to about fifty hours, alternatively from about one hour to about twenty-five hours. In embodiments, the reaction time may be any individual time in the above times or any smaller time ranges that are included in the above ranges. FIG. 3 illustrates examples of reaction time versus temperature. Without being limited by theory, it is to be understood that the higher the temperature, the less reaction time may be used. In embodiments, the reaction is allowed to occur for a sufficient time to substantially remove all of the contaminants (i.e., convert substantially all of the reactive sulfide to elemental sulfur). In some embodiments, the reaction produces substantially no foaming. And, in some embodiments, the reaction also does not generate ammonia. In an embodiemnt, the reaction is non-exothermic. In other embodiments, surfactants are not added to the contaminated water or methylmorpholine-N-oxide 20.

After the desired reaction time occurs (i.e., sulfide conversion is about complete), the water 35 (i.e., treated water) may be drawn off from vessel 10 and nonhazardous products 25 may also be removed from vessel 10. Water 35 may be sent to any desired location such as a water treatment plant. In embodiments, water 35 has no reactive sulfides. Nonhazardous products 25 include nonhazardous sulfur reaction products along with other native solids in vessel 10 (i.e., sludge). Nonhazardous products 25 may be removed from vessel 10 by an suitable means. In an embodiment, the means include a centrifuge. In embodiments, the liquid portion of the effluent passing from the centrifuge may then be routed to a treatment facility or any other desirable location.

In some embodiments (not illustrated), steam is not added to vessel 10.

In an embodiment as shown in FIG. 1, methylmorpholine-N-oxide water treatment method 5 may also include re-circulation 30. Re-circulation 30 is re-circulation of contaminated water. In some embodiments, contaminated water containing introduced methylmorpholine-N-oxide 20 (i.e., a mixture of contaminated water and methylmorpholine-N-oxide) is re-circulated. Without limitation, re-circulation 30 facilitates distribution of methylmorpholine-N-oxide 20 in contaminated water. In an embodiment, from about one volume of the toal amount of contaminated water and methylmorpholine-N-oxide solution in vessel 10 to about two vessel 10 volumes of the total amount of contaminated water and methylmorpholine-N-oxide solution in vessel 10 are re-circulated. In embodiments, re-circulation 30 may include re-circulation of any volume or range of volumes less than two.

Figure 2:
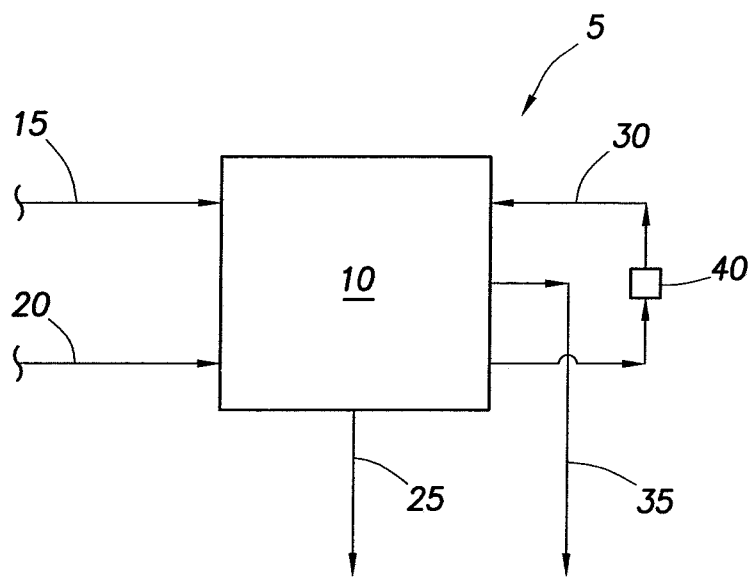
FIG. 2 illustrates an embodiment of a methylmorpholine-N-oxide water treatment method having a heat exchanger on the recycle.

In embodiments as shown in FIG. 2, methylmorpholine-N-oxide water treatment method 5 includes heat exchanger 40, which adds heat to re-circulation 30. Without limitation, adding the heat increases the reaction.

To further illustrate various illustrative embodiments of the present invention, the following examples are provided.

EXAMPLES

Example 1

A purpose of this Example 1 was to determine the extent of reaction of morpholine-N-oxide on $H_2S$ in sour water at varying mole ratios. The experiments of this Example 1 were conducted at 40° C. and 60° C.

At all mole ratios (morpholine-N-oxide:$H_2S$) down to and including 1.0:1.0, the destruction of $H_2S$ was complete at 60° C. after 24 hours. Elemental sulfur was a visible product. This S° was present as platelets ("flakes").

After 24 hours at 40° C., the reaction was complete only at a mole ratio of 3.0:1.0, although nearly complete reactions were recorded at ratios of 2.0:1.0 and 1.8:1.0. Reactions at lower mole ratios were variously incomplete and consistent with the lower loadings.

After 48 hours at 40° C., the reaction was complete at all mole ratios except for the lowest loading (1.0:1.0). The product S° was variously present as a milky suspension and flaked solids.

For the experiment, a pint of archived sour water at pH~8.5 was used with an $H_2S$ content at 9,985 mg/liter (0.293 M/lit). The molecular weight of the solid morpholine-N-oxide was 126.0.

A morpholine-N-oxide stock solution was prepared by dissolving 5.00 grams in 100.0 mls distilled water (0.397 Ma). To each of several screw-capped sample vials, 2.0 mls of the sour water and a dash of powdered iron rust were added. The vials were then diluted with ~15 mls of distilled water and the following volumes of morpholine-N-oxide were added.

TABLE 1

Sample Makeup
[Morpholine-N-oxide] = 0.397 M/lit
[$H_2S$] = 0.293 M/lit (@ pH~8.5)
~0.5 gm $Fe_2O_3 \cdot xH_2O$

| Volume morpholine-N-oxide stock | Mole ratio (N-oxide:$H_2S$) |
|---|---|
| 1.477 mls | 1.0:1 |
| 1.772 mls | 1.2:1 |
| 2.067 mls | 1.4:1 |
| 2.363 mls | 1.6:1 |
| 2.658 mls | 1.8:1 |
| 2.953 mls | 2.0:1 |
| 4.430 mls | 3.0:1 |

Three such series were prepared. Each series was treated as follows: series 1: heated at 40° C. for 24 hours (static), series 2: heated at 40° C. for 48 hours (static), series 3: heated at 60° C. for 24 hours (static).

At termination of the reaction periods, the entire contents of each reaction vial were emptied into 20 mls of sulfide anti-oxidant buffer, and each was titrated with 0.100 M/lit $Pb^{++}$, according to ULI Procedure LP1005. The results are shown below.

TABLE 2

Reaction of Morpholine-N-oxide on $H_2S$ for 24 Hours @ 40° C.

| Sample | mls $Pb^{++}$ | Gms $H_2S$ Titrated | Gms $H_2S$ Added | % Reacted |
|---|---|---|---|---|
| 1.0:1 | 1.9 | 0.00019 | 0.000585 | 68% |
| 1.2:1 | 1.8 | 0.00018 | 0.000585 | 69% |
| 1.4:1 | 1.7 | 0.00017 | 0.000585 | 71% |
| 1.6:1 | 0.7 | 0.00007 | 0.000585 | 88% |
| 1.8:1 | 0.4 | 0.00004 | 0.000585 | 93% |
| 2.0:1 | 0.3 | 0.00003 | 0.000585 | 95% |
| 3.0:1 | 0.0 | 0.00000 | 0.000585 | 100% |

TABLE 3

Reaction of Morpholine-N-oxide on $H_2S$ for 48 Hours @ 40° C.

| Sample | mls $Pb^{++}$ | Gms $H_2S$ Titrated | Gms $H_2S$ Added | % Reacted |
|---|---|---|---|---|
| 1.0:1 | 0.4 | 0.00004 | 0.000585 | 93% |
| 1.2:1 | 0.0 | 0.00000 | 0.000585 | 100% |
| 1.4:1 | 0.0 | 0.00000 | 0.000585 | 100% |
| 1.6:1 | 0.0 | 0.00000 | 0.000585 | 100% |
| 1.8:1 | 0.0 | 0.00000 | 0.000585 | 100% |
| 2.0:1 | 0.0 | 0.00000 | 0.000585 | 100% |
| 3.0:1 | 0.0 | 0.00000 | 0.000585 | 100% |

Elemental sulfur, present as small platelets, had been precipitated during reaction.

TABLE 4

Reaction of Morpholine-N-oxide on $H_2S$ for 24 Hours @ 60° C.

| Sample | mls $Pb^{++}$ | Gms $H_2S$ Titrated | Gms $H_2S$ Added | % Reacted |
|---|---|---|---|---|
| 1.0:1 | 0.0 | 0.00000 | 0.000585 | 100% |
| 1.2:1 | 0.0 | 0.00000 | 0.000585 | 100% |
| 1.4:1 | 0.0 | 0.00000 | 0.000585 | 100% |
| 1.6:1 | 0.0 | 0.00000 | 0.000585 | 100% |
| 1.8:1 | 0.0 | 0.00000 | 0.000585 | 100% |
| 2.0:1 | 0.0 | 0.00000 | 0.000585 | 100% |
| 3.0:1 | 0.0 | 0.00000 | 0.000585 | 100% |

Elemental sulfur, present as small platelets, had been precipitated during reaction.

Example 2

A purpose of this example was to determine if a lower ratio than 1.0:1.0 of 4-methylmorpholine-N-oxide:sulfide will completely remove sulfide from solution. The experiments were conducted at 40° C. and 60° C.

At a mole ratio of 0.7:1.0 (N-oxide:sulfide), the oxidation and removal of sulfide appeared to be 98%-99% complete.

A pint of archived sour water at pH-8.5 was used and that had an $H_2S$ content at 8,016 mg/liter (0.250 M/lit). A sample of solid 4-methylmorpholine-N-oxide was determined to have a molecular weight of 126.0.

A 4-methylmorpholine-N-oxide stock solution was prepared by dissolving 5.00 grams in 100.0 mls distilled water (0.397 M/lit). To each of four screw-capped sample vials, 2.0 mls of the sour water and a dash of powdered iron rust were added. The vials were diluted to ~20 mls with distilled water after adding 0.822 mls of 4-methylmorpholine-N-oxide, which amounted to a reaction ratio of 0.7:1.0.

Two of the samples were placed in a 40° C. bath for a reaction time of 48 hours. The other two were placed in a 60° C. bath for 24 hours. At termination of the reaction periods, the entire contents of a reaction vial from each bath were emptied into 20 mls of sulfide anti-oxidant buffer and each was titrated with 0.100 M/lit $Pb^{++}$, according to ULI Procedure LP1005.

The sample reacted at 40° C. required 0.10 mls of the Pb titrant, and the sample reacted at 60° C. required 0.05 mls. These analysis results calculated to 99% and 98% destruction of sulfide in the tests.

The second samples from these reactions were acidified with $H_2SO_4$. This was done in order to determine if there was any odor of residual $H_2S$. There was no odor of $H_2S$. Instead, there was the unmistakable odor of $SO_2$. A common reaction product of N-oxides with $S^=$ is thiosulfate. When thiosulfate is acidified, it disproportionates, forming $SO_2$.

Elemental sulfur, present as small platelets, had been formed during both reactions.

Example 3

Two large sour water tanks (about 20,000 $m^3$) were respectively 80% and 75% filled. Methylmorpholine-N-oxide with added temperature of 50° C. was found to reduce hydrogen sulfide to 0 ppm in 19 hours or less.

During the course of testing, discoveries were made about the catalytic effect of the voluminous corrosion solids in the tank. When such solids were present, methylmorpholine-N-oxide trials at ambient temperatures were found to be complete with hydrogen sulfide at 0 ppm after 24 hours treatment time. Other trials where the solids were removed prior to methylmorpholine-N-oxide treatment demonstrated that methylmorpholine-N-oxide reduced hydrogen sulfide to 0 ppm in six days at ambient conditions.

A sample of the first tank was taken and found to be black from suspended corrosion solids ($Fe_2O_3$+FeS). Various analyses were conducted in order to determine $H_2S$ content so that a methylmorpholine-N-oxide dose could be calculated. Prior readings were 800-900 ppm $H_2S$. A test using a Chemets sulfide colorimetric test kit estimated 400-500 ppm $H_2S$. Iodometric titration gave an $H_2S$ result of 600-700 ppm on the whole sample, and 400-500 ppm $H_2S$ on filtered sample.

The first demonstration was performed under standard conditions where treatments were assisted by heating at 50° C. Two different dosage levels were prepared using newly-made as well as eight month old formulation. One sample was run at ambient conditions. The test make-ups are below in Table 5.

TABLE 5

| First Tank | methylmorpholine-N-oxide: $H_2S$ mole ratio | Temp (° C.) | Start |
|---|---|---|---|
| 15 | 1.5:1 | 50 | 14:30 |
| 15 | 3:1 | 50 | 14:30 |
| 15 | 3:1 | 50 | 14:30 |
| 15 | 3:1 | 50 | 14:30 |

After 19 hours under the test conditions described above, the heated samples were observed to be completely reacted ($H_2S$=0 ppm). Also, the ambient sample was mostly reacted as evidenced by a cloudy yellow solution, which is typical for that course of the reaction.

Verification of the completion of $H_2S$ oxidation was seen in the lead acetate test strips. A dark strip was untreated, the clear strip included the three heated samples with $H_2S$=0 ppm, and another strip was the ambient sample that was seen to be much lighter. A subsequent test with Chemets colorimetric sulfide kit indicated the $H_2S$ levels in the ambient sample to be well below 100 ppm $H_2S$.

The ambient tests were surprising. This test suggested that the presence of significant amounts of corrosion material were such a sufficient catalyst for timely methylmorpholine-N-oxide reaction that heat was not necessary.

Lab trials were initiated to study the effectiveness of methylmorpholine-N-oxide at low dose rates and under ambient conditions. The sample array was intended to study the reaction rate of methylmorpholine-N-oxide with and without the catalytic solids and also varying dose rates. One sample represented the most extreme test of methylmorpholine-N-oxide—ambient conditions with no solids present and a methylmorpholine-N-oxide: $H_2S$ ratio of 1:1 (i.e., the lowest theoretical dose rate possible). Test parameters were summarized in Table 6.

TABLE 6

| Mole ratio methylmorpholine-N-oxide:$H_2S$ | Solids Level | Temperature | Start |
|---|---|---|---|
| 1:1 | Minimal | Ambient | 10:00 |
| 1.5:1 | Minimal | Ambient | 10:00 |
| 1.5:1 | Abundant-Sx Shaken | Ambient | 10:00 |

After 24 hours of exposure, methylmorpholine-N-oxide was found to produce complete eradication of $H_2S$ in the sample with solids as evidenced. This was consistent with the ambient test with solids above. Also, the higher dose sample with no solids looked to be turning a darker shade of yellow, which indicated some initial progress in reaction.

Both of the samples with no solids present were also seen to progressively react with all the H₂S as well, at much longer reaction times. A summary of the results is included in Table 7.

TABLE 7

| Solids Present | Mole Ratio | Time to $H_2S$ = 0 ppm |
|---|---|---|
| Yes | 1.5:1 | 24 hours |
| No | 1.5:1 | 6 days |
| No | 1:1 (theoretical minimum) | 12 days |

Figure 4:
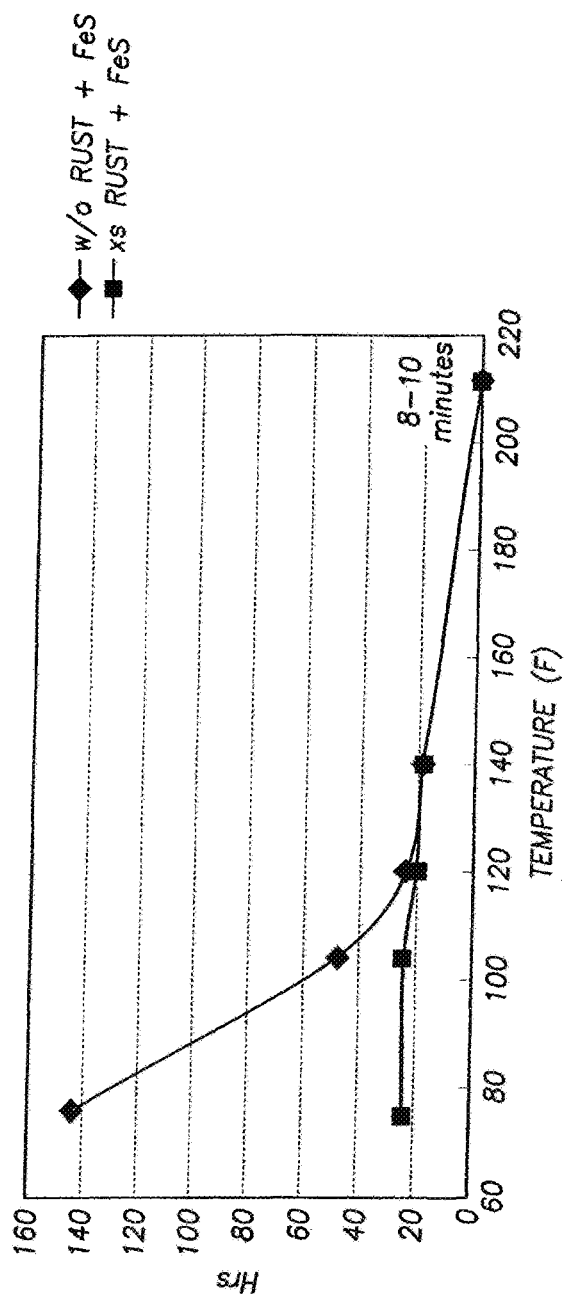
FIG. 4 illustrates reaction time versus temperature.

FIG. 4 illustrates a complete performance summary of methylmorpholine-N-oxide for total H₂S eradication under different conditions.

Although the present invention and its advantages have been described in detail, it should be understood that various changes, substitutions and alterations may be made herein without departing from the spirit and scope of the invention as defined by the appended claims.

What is claimed is:

1. A method for treating contaminants in water, comprising:
   (A) contacting the water with a methylmorpholine-N-oxide solution while in a presence, of iron oxide, wherein the contaminants comprise hydrogen sulfide, iron sulfides, or any combinations thereof, wherein the water is in a vessel, wherein the methylmorpholine-N-oxide solution is introduced to the vessel to contact the water, wherein the vessel is a tank, wherein the iron oxide comprises $Fe_2O_3 \cdot 7H_2O$, $Fe_2O_3 \cdot 10H_2O$, or any combination thereof, wherein the methylmorpholine-N-oxide solution is introduced to the vessel by a drum pump, a tank truck, or any combination thereof;
   (B) treating the water by allowing a reaction to occur between the methylmorpholine N-oxide and the contaminants in the presence of the iron oxide to produce elemental sulfur and thiosulphate reaction products; and
   (C) removing the elemental sulfur and the thiosulphate reaction products from the water by centrifuge.

2. The method of claim 1, wherein the methylmorpholine-N-oxide solution comprises between about 1 weight volume % and about 60 weight volume % methylmorpholine-N-oxide.

3. The method of claim 1, wherein the methylmorpholine-N-oxide solution is not heated before introduction to the vessel.

4. The method of claim 1, wherein a molar ratio of methylmorpholine-N-oxide to contaminant is about 1.0 mole methylmorpholine-N-oxide:1.0 mole contaminant to about 3.0 moles methylmorpholine-N-oxide:1.0 mole contaminant.

5. The method of claim 1, wherein the methylmorpholine-N-oxide solution reacts with the contaminants from about one hour to about fifty hours.

6. The method of claim 1, wherein treating the contaminated water provides a treated water, wherein the treated water comprises 0 ppm hydrogen sulfide.

7. The method of claim 1, wherein the reaction is irreversible.

8. A method for treating contaminants in water, comprising:
   (A) contacting the water with a methylmorpholine-N-oxide solution while in a presence of iron oxide, wherein the contaminants comprise hydrogen sulfide, iron sulfides, or any combinations thereof, wherein the iron oxide is present in the water in an amount from about 100 ppm to about 1,000 ppm iron oxide;
   (B) treating the water by allowing the methylmorpholine-N-oxide to react with the contaminants in the presence of the iron oxide to produce elemental sulfur and thiosulfate reaction products, further comprising introducing steam to contact the water, wherein introducing the steam to contact the water increases a temperature of the water; and
   (C) removing the elemental sulfa and the thiosulfate reaction products from the water.

9. The method of claim 8, wherein the methylmorpholine-N-oxide solution comprises between about 1 weight volume % and about 60 weight volume % methylmorpholine-N-oxide.

10. The method of claim 8, wherein the steam comprises 150 psig steam or less.

11. The method of claim 8, wherein the iron oxide comprises ferrous or ferric oxides that are hydrated.

12. The method of claim 8, wherein the methylmorpholine-N-oxide solution reacts with the contaminants from about one hour to about fifty hours.

13. The method of claim 8, wherein the methylmorpholine-N-oxide solution is not heated before the contacting step (A).

14. The method of claim 8, wherein treating the water provides a treated water, and wherein the treated water comprises 0 ppm hydrogen sulfide.

15. The method of claim 8, wherein the reaction is irreversible.

16. A method for treating contaminants in water, comprising:
   (A) contacting the water with a methylmorpholine-N-oxide solution while in a presence of iron oxide, wherein the contaminants comprise hydrogen sulfide, iron sulfides, or any combinations thereof;
   (B) treating the water by allowing the methylmorpholine-N-oxide to react with the contaminants in the presence of the iron oxide to produce elemental sulfur and thiosulfate reaction products; and
   (C) removing the elemental sulfur and thiosulfate reaction products from the water, further comprising recirculating a mixture of the water and the methylmorpholine-N-oxide solution, wherein the re-circulating comprises re-circulating between about one volume of a total amount of the mixture of the water and the methylmorpholine-N-oxide to about two volumes of the total amount of the mixture the water and the methylmorpholine-N-oxide.

17. The method of claim 16, wherein the re-circulating further comprises heating the water and the methylmorpholine-N-oxide.

18. The method of claim 17, wherein the heating comprises a heat exchanger providing heat to the water and the methylmorpholine-N-oxide.

19. The method of claim 17, wherein heating the water and methylmorpholine-N-oxide solution decreases reaction time.

20. The method of claim 16, wherein the reaction is irreversible.

* * * * *